United States Patent [19]

Dunbar et al.

[11] Patent Number: 4,661,520

[45] Date of Patent: Apr. 28, 1987

[54] CYANOGUANIDINE USEFUL AS AN ANIMAL GROWTH PROMOTING AGENT

[75] Inventors: Joseph E. Dunbar; David M. Hedstrand, both of Midland, Mich.; Kimiaki Maruyama, Hastings, Nebr.

[73] Assignee: The Dow Chemical Company, Midland, Mich.

[21] Appl. No.: 641,809

[22] Filed: Aug. 17, 1984

[51] Int. Cl.$^4$ .................. A61K 31/17; C07C 129/14
[52] U.S. Cl. ........................ 514/609; 564/104
[58] Field of Search ............... 564/104; 424/322; 514/609

[56] References Cited

U.S. PATENT DOCUMENTS

| | | | |
|---|---|---|---|
| 3,248,426 | 4/1966 | Dvornik | 260/564 |
| 3,344,186 | 9/1967 | Augstein et al. | 260/564 |
| 3,953,506 | 4/1976 | Spicer et al. | 260/553 A |
| 3,953,606 | 4/1976 | Spicer et al. | 424/322 |
| 4,005,140 | 1/1977 | Spicer et al. | 260/553 A |
| 4,041,070 | 8/1977 | Asato et al. | 260/553 A |
| 4,049,717 | 9/1977 | Asato | 260/575 |
| 4,051,183 | 9/1977 | Asato | 260/553 A |
| 4,062,856 | 12/1977 | Spicer et al. | 260/295.5 B |
| 4,072,711 | 2/1978 | Asato et al. | 260/554 |
| 4,076,952 | 2/1978 | Asato et al. | 560/28 |
| 4,088,786 | 5/1978 | Asato et al. | 424/322 |
| 4,089,976 | 5/1978 | Asato | 424/322 |
| 4,091,018 | 5/1978 | Asato | 260/562 R |
| 4,185,091 | 1/1980 | Knüsel et al. | 424/118 |
| 4,199,510 | 4/1980 | Zwieg et al. | 260/326 S |
| 4,209,518 | 6/1980 | Mine et al. | 514/249 |
| 4,287,346 | 9/1981 | Tanaka et al. | 546/330 |
| 4,327,217 | 4/1982 | Tanaka et al. | 546/281 |
| 4,333,923 | 6/1982 | Beck et al. | 424/115 |
| 4,363,921 | 12/1982 | Tanaka et al. | 549/74 |
| 4,365,067 | 12/1982 | Fugimoto et al. | 548/342 |
| 4,396,764 | 8/1983 | Tanaka et al. | 544/124 |
| 4,405,644 | 9/1983 | Kabbe et al. | 424/322 |

FOREIGN PATENT DOCUMENTS

| | | | |
|---|---|---|---|
| 516685 | 9/1955 | Canada | 564/104 |
| 599722 | 3/1948 | United Kingdom . | |
| 800869 | 9/1958 | United Kingdom . | |
| 842322 | 7/1960 | United Kingdom . | |

OTHER PUBLICATIONS

Grigat, E. and Pütter, R. *Chem. Ber.* 98, p. 2619 (1965).
Grigat, E. and Pütter, R. *Chem. Ber.* 99, p. 958 (1966).
Grigat, E. and Pütter, R. *Angew. Chem. Int. Ed.* 6, p. 206 (1967).
Grigat, E. and Pütter, R. *Angew. Chem. Int. Ed.* 11, p. 949 (1972).
Turner, R. W. *Synthesis*, p. 332 (1975).

*Primary Examiner*—Anton H. Sutto
*Attorney, Agent, or Firm*—Thomas R. Savitsky; Kenneth L. Loertscher

[57] ABSTRACT

This invention relates to a novel cyanoguanidine compound, N'-cyano-N-(1,2,3,4-tetrahydro-1-naphthyl)-guanidine, which is useful as an animal growth promoting agent.

3 Claims, No Drawings

CYANOGUANIDINE USEFUL AS AN ANIMAL GROWTH PROMOTING AGENT

SUMMARY OF THE INVENTION

This invention is directed to a novel cyanoguanidine compound, N'-cyano-N-(1,2,3,4-tetrahydro-1-naphthyl)guanidine, corresponding to the formula:

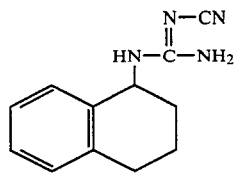

This invention is also directed to a method of promoting the growth of animals in need thereof which comprises administering an effective amount of the compound of Formula I to said animals.

This invention is also directed to an animal feed composition comprising the compound of Formula I in admixture with standard animal feed.

As used herein, the term "animals" refers to those animals in which it is desirable to increase growth rate and/or feed conversion efficiency, such as poultry, swine, cattle or sheep; the term "effective amount" refers to that amount of the compound sufficient to increase the growth rate and/or the feed conversion efficiency of the treated animals without resulting in any significant adverse side effects; the term "aryl" refers to a monocyclic or bicyclic carbocyclic aryl, such as phenyl or naphthyl, which can optionally be substituted with at least one electron withdrawing substituent such as chloro, bromo, fluoro, nitro, or the like.

DETAILED DESCRIPTION OF THE INVENTION

The novel cyanoguanidine compound represented by Formula I can be prepared by one of three methods (Methods A, B and C) as follows:

Method A 1,2,3,4-Tetrahydro-1-naphthylamine hydrochloride and sodium dicyanamide are contacted and mixed in a suitable solvent such as water under conditions at which the desired product is formed. For example, the desired compound is formed when the mixture is heated at about 95° C. to 100° C. for about 2 to 18 hours. The reaction mixture is then cooled and extracted with a suitable low molecular weight chlorinated organic solvent such as methylene chloride or chloroform. Typically, equimolar amounts of the reactants are employed, however, the molar proportion of the reactants is not critical. The reaction is illustrated as follows:

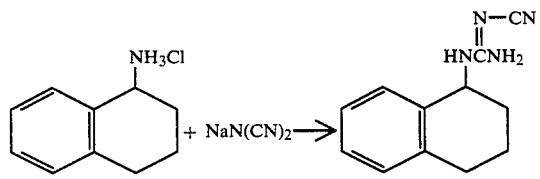

Methods B and C require N-cyano-O-arylisourea as a starting material. N-cyano-O-arylisourea can be prepared by contacting and mixing cyanamide with an appropriate aryl cyanate in ether in the presence of a catalytic amount of triethylamine by the method of Grigat, E., and Pütter, R., Chem. Ber., 98, 2619-2630 (1965).

Method B

N-cyano-O-arylisourea and 1,2,3,4-tetrahydro-1-naphthylamine are contacted and mixed under conditions at which the desired product is formed. For example, the reaction proceeds when the reaction mixture is heated at about 200° C. to 220° C. for a time sufficient to obtain the desired product, generally 8 to 10 minutes is sufficient. Typically excess amine is used, however, the molar proportion of reactants is not critical. The desired product can be isolated using standard procedures, for example, by chromatography employing a suitable solvent system of increasing polarity.

Method C

N-cyano-O-arylisourea and 1,2,3,4-tetrahydro-1-naphthylamine are contacted and mixed in a suitable organic solvent such as chloroform under conditions at which the desired product is formed. For example, the desired compound is formed when the reactants are heated to about reflux temperature in the presence of a suitable organic solvent for a time sufficient to obtain the desired compound, generally a reaction time of about 1 hour to 2 days is sufficient. A preferred method is to use the minimum amount of solvent necessary to keep the reactants in solution during the reaction period. Typically, equimolar amounts of reactants are employed; however, the molar proportion is not critical. After the reaction period, the reaction mixture is cooled to about room temperature and then treated with a suitable amount of an appropriate non-polar solvent such as toluene, benzene, or hexane to promote crystallization of the desired product which is then recovered employing standard procedures. Generally, an additional amount of the desired product can be obtained after concentrating the mother liquor slightly.

Methods B and C can be illustrated as follows (the reaction with regard to Method C taking place in the presence of a suitable organic solvent):

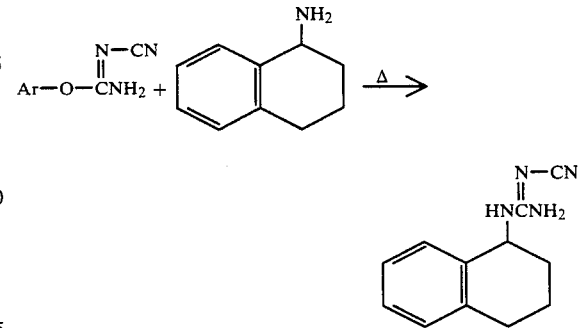

wherein Ar represents aryl.

The cyanoguanidine of this invention, N'-cyano-N-(1,2,3,4-tetrahydro-1-naphthyl)guanidine, can be administered in a growth promoting amount to an animal. The compound of this invention can be administered to animals by conventional methods appreciated by one skilled in the art (for example, see the methods taught in U.S. Pat. Nos. 4,185,091; 4,209,518; and 4,333,923; incorporated herein by reference). When administered in the feed of the animals, usually about 1.3 to 90 milligrams of the compound per kilogram of animal body weight per day is effective in promoting the growth of animals. The exact amount of the compound to be employed will vary depending upon factors such as species of animal, or the size, weight, age, and health of the animal. In particular cases, the concentration to be administered may be determined by conventional dose titration techniques.

The present invention is further illustrated by the following examples; however, these examples should not be interpreted as a limitation upon the scope of the present invention.

EXAMPLE 1

Preparation of N'-cyano-N-(1,2,3,4-tetrahydro-1-naphthyl)guanidine (Method A).

A solution of 18.4 grams (g) of 1,2,3,4-tetrahydro-1-naphthylamine hydrochloride and 8.90 g of sodium dicyanamide in 220 milliliters (ml) of water was heated at 95° C. (steam bath) for 21 hours, after which time a viscous oil had precipitated from the hot solution. The reaction mixture was then cooled and extracted with methylene chloride. The methylene chloride extract was dried over anhydrous sodium sulfate and the sodium sulfate removed by filtration. The methylene chloride was then removed by evaporation in vacuo, leaving the crude product as a pale yellow gum. The gum was crystallized from isopropyl acetate to give an off-white, crystalline solid, melting point (mp) 153.5°–156.5° C. Recrystallization from aqueous ethanol gave 3.87 g of N'-cyano-N-(1,2,3,4-tetrahydro-1-naphthyl)guanidine as a white, crystalline solid, mp 157°–158° C.

| Analysis | C | H | N |
|---|---|---|---|
| Calculated for $C_{12}H_{14}N_4$: | 67.26 | 6.59 | 26.15 |
| Found: | 67.0 | 6.57 | 26.16 |

EXAMPLE 2

Preparation of N'-cyano-N-(1,2,3,4-tetrahydro-1-naphthyl)guanidine (Method B):

A 25 ml round bottom flask containing a mixture of 4.8 g of N-cyano-O-phenylisourea and 6 g of 1,2,3,4-tetrahydro-1-naphthylamine was placed in an oil bath preheated to 190° C. The bath temperature was raised to 220° C. over 20 minutes and maintained at 220° C. for 8 minutes. Upon cooling, the reaction mixture had a glass-like appearance. The product was isolated from the reaction mixture by thorough shaking of the reaction mixture with ether to remove the remaining starting materials and phenol, and decanting the ether solution which left the crude product as a white gummy residue. The crude product was further purified by chromatography on a column packed with silica gel and eluting initially with toluene then with toluene-ethyl acetate mixtures with gradual increase in the ethyl acetate content. This gave 4.61 g of the desired compound that had satisfactory data in spectroscopic analysis.

EXAMPLE 3

Preparation of N'-cyano-N-(1,2,3,4-tetrahydro-1-naphthyl)guanidine (Method C):

A mixture of 1.3 g of N-cyano-O-phenylisourea and 1.2 g of 1,2,3,4-tetrahydro-1-naphthylamine in 5 ml of chloroform was heated at reflux in an oil bath. Disappearance of the isourea was monitored by thin layer chromatography analysis. After 30 hours, the resulting thick solution was treated with 5 ml of toluene and allowed to stand at room temperature which resulted in the crystallization of the desired product. The supernatant solution was withdrawn and the product washed with toluene (10 ml). Upon drying under vacuum, 0.91 g of the desired compound was obtained. A second crop of crystals was collected after concentrating the mother liquor slightly. Total yield of N'-cyano-N-(1,2,3,4-tetrahydro-1-naphthyl)guanidine was 1.29 g, mp 153°–155° C.

| Analysis | C | H | N |
|---|---|---|---|
| Calculated for $C_{12}H_{14}N_4$: | 67.26 | 6.59 | 26.15 |
| Found: | 67.5 | 6.65 | 26.23 |

EXAMPLE 4

The animal growth promoting activity of the novel compound of this invention was illustrated as follows:

CD-1 male mice from Charles River Breeding Laboratories, Portage, Mich. were received at about 3 weeks of age (14–16 grams). Upon arrival the mice were randomly assigned to groups of 16–20 and housed in plastic cages and acclimated on Purina Rodent Laboratory Chow No. 5002 ® (the stock diet) for three days. On the fourth day the mice were weighed and mice of the upper and lower weight extremes were discarded. The remaining mice were randomly assigned in groups of four to plastic cages. At this time, the stock diet was replaced with a 23% casein diet for the remaining 5 days of the acclimation period. Each cage of four mice was then randomly assigned to either the treatment group or the control group. Food and water were available ad libitum. Animals were housed in air conditioned rooms (72° F. to 76° F.) with automatically controlled lights (12 hours on, 12 hours off). During the treatment period the test mice in the control group were fed the 23% casein diet and test mice in the treatment group were fed the 23% casein diet mixed with the test compound, N'-cyano-N-(1,2,3,4-tetrahydro-1-naphthyl)-guanidine. The concentration of the test compound, N'-cyano-N-(1,2,3,4-tetrahydro-1-naphthyl)guanidine, was 75 parts per million (ppm) in the 23% casein diet.

The control and treatment groups each contained nine cages of four mice (i.e., 36 mice per group). The treatment period was nine days. During the first three days of the treatment period the mice were weighed daily and an average weight determined for each group (the initial average weight). The mice were again weighed daily during the last three days of the treatment period and an average weight determined (the final average weight). The final average weights and the initial average weights were used to calculate the average daily weight gain for the respective control group and treatment group. The percent weight gain was then calculated as shown in Table 1.

| Composition of 23% casein diet: | |
|---|---|
| Casein | 23.0% |
| Dextrose | 31.5% |
| Starch | 31.5% |
| Corn Oil | 5.0% |
| Mineral Mix (AIN76) | 3.5% |
| Vitamin Mix (AIN76A) | 1.0% |
| Cellulose | 4.0% |
| d,1-Methionine | 0.3% |
| Choline Bitartrate | 0.2% |

TABLE 1

| Compound | Dietary Level ppm | *Percent Weight Gain |
| --- | --- | --- |
| N'—cyano-N—(1,2,3,4-tetrahydro-1-naphthyl)guanidine | 75 | 119 |

*Percent Weight Gain = $\dfrac{\text{average daily weight gain treated group}}{\text{average daily weight gain control group}} \times 100$ The compound of this invention has demonstrated herbicidal activity in standard tests.

What is claimed is:

1. A compound of the formula:

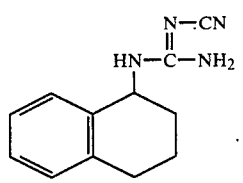

2. A method for promoting the growth of animals comprising administering to said animals an effective amount of a compound of the formula:

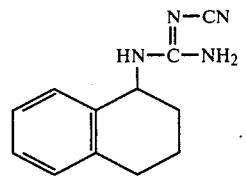

3. An animal feed composition suitable for promoting the growth of animals which comprises a mixture of animal feed and an effective amount of a compound of the formula:

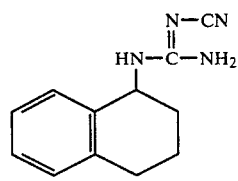

* * * * *